(12) United States Patent
Hayden et al.

(10) Patent No.: US 9,290,751 B2
(45) Date of Patent: Mar. 22, 2016

(54) LPL VARIANT THERAPEUTICS

(71) Applicants: Michael R. Hayden, Vancouver (CA); John P. Kastelein, Hauwewrt (NL)

(72) Inventors: Michael R. Hayden, Vancouver (CA); John P. Kastelein, Hauwewrt (NL)

(73) Assignees: Michael R. Hayden, Vancouver, B.C. (CA); John P. Kastelein, Hauwewrt (NL); Katherine Excoffon, Davenport, IA (US)

( * ) Notice: Subject to any disclaimer, the term of this patent is extended or adjusted under 35 U.S.C. 154(b) by 0 days.

(21) Appl. No.: 14/324,151

(22) Filed: Jul. 4, 2014

(65) Prior Publication Data

US 2015/0030581 A1 Jan. 29, 2015

Related U.S. Application Data

(63) Continuation of application No. 13/850,203, filed on Mar. 25, 2013, now abandoned.

(51) Int. Cl.
*C12N 9/20* (2006.01)
*A61K 48/00* (2006.01)

(52) U.S. Cl.
CPC ............... *C12N 9/20* (2013.01); *A61K 48/005* (2013.01); *C12Y 301/01034* (2013.01); *A61K 48/00* (2013.01); *C12N 2710/10343* (2013.01); *C12N 2710/10371* (2013.01)

(58) Field of Classification Search
CPC ....................................................... C12N 9/20
See application file for complete search history.

*Primary Examiner* — Amber D Steele
(74) *Attorney, Agent, or Firm* — Jeffrey J. King; Patent Networks Law Group PLLC

(57) ABSTRACT

The invention provides for the use of a therapeutic derived from a truncated lipoprotein lipase protein (LPL S447X), including nucleic acids encoding such proteins, for the treatment of conditions including LPL responsive conditions, such as cardiovascular disease, hypertension, LPL deficiency, high triglyceride levels, low HDL-cholesterol levels or atherosclerosis.

11 Claims, 3 Drawing Sheets

Figure 1

LPL S447X 1-446 Peptide:

```
                                adq rrdfidiesk falrtpedta edtchlipgv  33
aesvatchfn hssktfmvih gwtvtgmyes wvpklvaaly krepdsnviv vdwlsraqeh  93
ypvsagytkl vgqdvarfin wmeeefnypl dnvhllgysl gahaagiags ltnkkvnrit 153
gldpagpnfe yaeapsrlsp ddadfvdvlh tftrgspgrs igiqkpvghv diypnggtfq 213
pgcnigeair viaerglgdv dqlvkcsher sihlfidsll neenpskayr csskeafekg 273
lclscrknrc nnlgyeinkv rakrsskmyl ktrsqmpykv fhyqvkihfs gtesethtnq 333
afeislygtv aesenipftl pevstnktys fliytevdig ellmlklkwk sdsyfswsdw 393
wsspgfaiqk irvkagetqk kvifcsrekv shlqkgkapa vfvkchdksl nkk        446
```

Figure 2

Mature LPL Peptide 1-448:

```
                                adq rrdfidiesk falrtpedta edtchlipgv  33
aesvatchfn hssktfmvih gwtvtgmyes wvpklvaaly krepdsnviv vdwlsraqeh  93
ypvsagytkl vgqdvarfin wmeeefnypl dnvhllgysl gahaagiags ltnkkvnrit 153
gldpagpnfe yaeapsrlsp ddadfvdvlh tftrgspgrs igiqkpvghv diypnggtfq 213
pgcnigeair viaerglgdv dqlvkcsher sihlfidsll neenpskayr csskeafekg 273
lclscrknrc nnlgyeinkv rakrsskmyl ktrsqmpykv fhyqvkihfs gtesethtnq 333
afeislygtv aesenipftl pevstnktys fliytevdig ellmlklkwk sdsyfswsdw 393
wsspgfaiqk irvkagetqk kvifcsrekv shlqkgkapa vfvkchdksl nkksg      448
```

Figure 3

Pre-LPL Peptide: 1-27 Signal Peptide (boxed) and Mature Peptide 28-475:

```
  1 meskallvlt lavwlqslta srggvaa adq rrdfidiesk falrtpedta edtchlipgv
 61 aesvatchfn hssktfmvih gwtvtgmyes wvpklvaaly krepdsnviv vdwlsraqeh
121 ypvsagytkl vgqdvarfin wmeeefnypl dnvhllgysl gahaagiags ltnkkvnrit
181 gldpagpnfe yaeapsrlsp ddadfvdvlh tftrgspgrs igiqkpvghv diypnggtfq
241 pgcnigeair viaerglgdv dqlvkcsher sihlfidsll neenpskayr csskeafekg
301 lclscrknrc nnlgyeinkv rakrsskmyl ktrsqmpykv fhyqvkihfs gtesethtnq
361 afeislygtv aesenipftl pevstnktys fliytevdig ellmlklkwk sdsyfswsdw
421 wsspgfaiqk irvkagetqk kvifcsrekv shlqkgkapa vfvkchdksl nkksg
```

Figure 4

LPL mRNA

```
   1 ccctcttcc tcctcctcaa gggaaagctg cccacttcta gctgccctgc catcccttt
  61 aaagggcgac ttgctcagcg ccaaaccgcg gctccagccc tctccagcct ccggctcagc
 121 cggctcatca gtcggtccgc gccttgcagc tcctccagag ggacgcgccc cgagatggag
 181 agcaaagccc tgctcgtgct gactctggcc gtgtggctcc agagtctgac cgcctcccgc
 241 ggaggggtgg ccgccgccga ccaaagaaga gattttatcg acatcgaaag taaatttgcc
 301 ctaaggaccc ctgaagacac agctgaggac acttgccacc tcattcccgg agtagcagag
 361 tccgtggcta cctgtcattt caatcacagc agcaaacct tcatggtgat ccatggctgg
 421 acggtaacag gaatgtatga gagttgggtg ccaaaacttg tggccgccct gtacaagaga
 481 gaaccagact ccaatgtcat tgtggtggac tggctgtcac gggctcagga cattaccca
 541 gtgtccgcgg ctacaccaa actggtggga caggatgtgg cccggtttat caactggatg
 601 gaggaggagt ttaactaccc tctggacaat gtccatctct tgggatacag ccttggagcc
 661 catgctgctg gcattgcagg aagtctgacc aataagaaag tcaacagaat tactggcctc
 721 gatccagctg gacctaactt tgagtatgca gaagcccga gtcgtctttc tcctgatgat
 781 gcagattttg tagacgtctt acacacattc accagagggt cccctggtcg aagcattgga
 841 atccagaaac cagttgggca tgttgacatt tacccgaatg gaggtacttt tcagccagga
 901 tgtaacattg gagaagctat ccgcgtgatt gcagagagag acttggaga tgtggaccag
 961 ctagtgaagt gctcccacga gcgctccatt catctcttca tcgactctct gttgaatgaa
1021 gaaaatccaa gtaaggccta caggtccagt tccaaggaag cctttgagaa agggctctgc
1081 ttgagttgta gaaagaaccg ctgcaacaat ctgggctatg agatcaataa agtcagagcc
1141 aaaagaagca gcaaaatgta cctgaagact cgttctcaga tgccctacaa agtcttccat
1201 taccaagtaa agattcattt ttctgggact gagagtgaaa cccataccaa tcaggccttt
1261 gagatttctc tgtatggcac cgtggccgag agtgagaaca tcccattcac tctgcctgaa
1321 gtttccacaa ataagaccta ctccttccta atttacacag aggtagatat tggagaacta
1381 ctcatgttga agctcaaatg gaagagtgat tcatacttta gctggtcaga ctggtggagc
1441 agtcccggct tcgccattca agatcaga gtaaaagcag gagagactca gaaaaggtg
1501 atcttctgtt ctaggagaa agtgtctcat ttgcagaaag gaaaggcacc tgcggtatt
1561 gtgaaatgcc atgacaagtc tctgaataag aagtcaggct gaaactgggc gaatctacag
1621 aacaaagaac ggcatgtgaa ttctgtgaag aatgaagtgg aggaagtaac ttttacaaaa
1681 catacccagt gttggggtg tttcaaaagt ggatttcct gaatattaat cccagcccta
1741 cccttgttag ttattttagg agacagtctc aagcactaaa aagtggctaa ttcaatttat
1801 ggggtatagt ggccaaatag cacatcctcc aacgttaaaa gacagtggat catgaaaagt
1861 gctgttttgt cctttgagaa agaaataatt gtttgagcgc agagtaaaat aaggctcctt
1921 catgtggcgt attgggccat agcctataat tggttagaac ctcctatttt aattggaatt
1981 ctggatcttt cggactgagg ccttctcaaa ctttactcta agtctccaag aatacagaaa
2041 atgcttttcc gcggcacgaa tcagactcat ctacacagca gtatgaatga tgttttagaa
2101 tgattccctc ttgctattgg aatgtggtcc agacgtcaac caggaacatg taacttggag
2161 agggacgaag aaagggtctg ataaacacag aggttttaaa cagtccctac cattggcctg
2221 catcatgaca aagttacaaa ttcaaggaga tataaaatct agatcaatta attcttaata
2281 ggctttatcg tttattgctt aatccctctc tccccttct ttttgtctc aagattatat
2341 tataataatg ttctctgggt aggtgttgaa aatgagcctg taatcctcag ctgacacata
2401 atttgaatgg tgcagaaaaa aaaagatac cgtaatttta ttattagatt ctccaaatga
2461 ttttcatcaa tttaaaatca ttcaatatct gacagttact cttcagtttt aggcttacct
2521 tggtcatgct tcagttgtac ttccagtgcg tctcttttgt tcctggcttt gacatgaaaa
2581 gataggtttg agttcaaatt ttgcattgtg tgagcttcta cagattttag acaaggaccg
2641 tttttactaa gtaaagggt ggagaggttc ctggggtgga ttcctaagca gtgcttgtaa
2701 accatcgcgt gcaatgagcc agatggagta ccatgagggt tgttatttgt tgttttaac
2761 aactaatcaa gagtgagtga acaactattt ataaactaga tctcctattt ttcagaatgc
2821 tcttctacgt ataaatatga aatgataaag atgtcaaata tctcagaggc tatagctggg
2881 aacccgactg tgaaagtatg tgatatctga acacatacta gaaagctctg catgtgtgtt
2941 gtccttcagc ataattcgga agggaaaaca gtcgatcaag ggatgtattg aacatgtcg
3001 gagtagaaat tgttcctgat gtgccagaac ttcgaccctt tctctgagag agatgatcgt
3061 gcctataaat agtaggacca atgttgtgat taacatcatc aggcttggaa tgaattctct
```

Figure 4 Continued

```
3121 ctaaaaataa aatgatgtat gatttgttgt tggcatcccc tttattaatt cattaaattt
3181 ctggatttgg gttgtgaccc agggtgcatt aacttaaaag attcactaaa gcagcacata
3241 gcactgggaa ctctggctcc gaaaaacttt gttatatata tcaaggatgt tctggcttta
3301 cattttattt attagctgta aatacatgtg tggatgtgta aatggagctt gtacatattg
3361 gaaaggtcat tgtggctatc tgcatttata aatgtgtggt gctaactgta tgtgtcttta
3421 tcagtgatgg tctcacagag ccaactcact cttatgaaat gggctttaac aaaacaagaa
3481 agaaacgtac ttaactgtgt gaagaaatgg aatcagcttt taataaaatt gacaacattt
3541 tattaccac
```

LPL VARIANT THERAPEUTICS

This application claims priority as a CONTINUATION of prior application U.S. CONTINUATION patent application Ser. No. 13/850,203, filed Mar. 25, 2013, U.S. CONTINUATION patent application Ser. No. 12/898,684, filed Oct. 5, 2010; U.S. CONTINUATION patent application Ser. No. 12/689,2.36, filed Jan. 19, 2010; U.S patent application Ser. No. 10/019,341, filed May 3, 2002, the disclosure of which priority is claimed and incorporated herein in their entirety by reference.

FIELD OF THE INVENTION

The invention is in the field of protein and nucleic acid therapeutics based on variants of lipoprotein lipase (LPL), including therapeutics delivered by gene therapy.

BACKGROUND OF THE INVENTION

Lipoprotein lipase (EC 3.1.1.34) is an important enzyme in the metabolism of triglyceride-rich lipoproteins. It is synthesized in the parenchymal cells of adipose tissue and skeletal and cardiac muscle, where it is transferred to binding sites at the vascular side of endothelial cells on the vascular endothelium. Current understanding is that LPL plays an important role in the regulation of lipoprotein and lipid metabolism, as follows. The noncovalently-linked glycosylated homodimer is thought to be transported to the vascular endothelium, where it binds heparan sulphate proteoglycans at the luminal surface. Subsequent catabolism of triglycerides from both chylomicrons (CM) and very low density lipoproteins (VLDL) is understood to allow the uptake and utilization of the free fatty acids and glycerol for energy and storage in muscle and adipose tissue respectively. Chylomicron and VLDL remnants may either be used in high density lipoprotein (HDL) or low density lipoprotein (LDL) particle formation respectively, or taken up by the liver and repackaged into new VLDL particles. LPL has an obligatory requirement for its activator apolipoprotein (apo) CII, a small protein of 79 amino acids that is present on CM and VLDL particles. Inhibitors of LPL include free fatty acids, apo CIII, and possibly apo E. Another inhibitor is high concentrations of salt (1M NaCl).

Although the cellular origin of LPL in the circulation is unclear, and may represent an accumulation from several tissue sources, its primary site of action is understood to be at the luminal surface of the vascular endothelium. Due to its non-covalent interaction with heparan sulphate proteoglycans, LPL may be displaced into the plasma by an intravenous bolus injection of heparin. Thus, LPL activity and protein levels can be simply assessed by taking a small sample of post-heparin plasma (PHP). Aliquots of this PHP can then be used in either a synthetic, radiolabled triglyceride (TG) assay for lipolytic activity or be measured by LPL specific antibodies for protein levels. Lipid measures may be performed in pre-heparin samples since the release of LPL may cause rapid lipolysis of the triglyceride in the sample.

Complete LPL deficiency occurs in approximately 1 in $10^6$ persons, and the frequency is much higher in the French Canadian population where it may occur in up to 1 in 5000 individuals. The clinical manifestations of complete LPL deficiency in humans stem from infancy with a failure to thrive, colicky abdominal pain, hepatosplenomegaly, chylomicronemia characterized by lactescent plasma, eruptive xanthomata, lipemia retinalis and life threatening pancreatitis. Lipid lowering drugs are ineffective and even rigid dietary restrictions are often poorly tolerated. The development of therapies for LPL deficiency would represent a major advance for persons suffering from this disorder.

Recently, patients with mutations in the LPL gene which result in partial defects in LPL catalytic function have been identified and, in fact, are very common in the general population. Collectively, known mutations resulting in partial catalytic defects in LPL are now estimated to occur with a frequency of between 5-7% in the general population. The clinical presentation may be quiescent, evident only by marginally elevated triglyceride levels in the non-stressed state, with profound hypertriglyceridemia triggered by factors such as normal pregnancy, obesity or diabetes. Postprandial metabolic studies have been performed on individuals heterozygous for mutations in the LPL gene, demonstrating an unmasking of the lipolytic defect after a fat challenge, resulting in prolonged post-prandial lipemia and significant disturbances in lipoprotein levels and composition. There is also evidence that specific mutations that alter, but do not abolish, LPL activity, such as Asn291Ser, Asp9Asn, exist commonly in the general population (Reymer et al., *Nat. Genet.* 1995, 10:28-33; Gagné et al., *Arterioscl. Thromb.* 1994, 14(8):1250-1257). The significance of this is not yet fully understood although they are implicated in atherosclerosis susceptibility. A mutation that introduces a termination codon at position 447 in place of a serine codon (Ser447Ter or S447X) has been associated with decreased TG and increased HDL-cholesterol levels (Hokanson, 1997, International Journal of Clinical and Laboratory Research 27, 24-34; Gagné et al., *Arteriosci. Thromb.* 1994, 14(8):1250-1257; Mattu et al., 1994, Arteriosclerosis and Thrombosis 14, 1090-1097; Kuivenhoven et al., 1997, Arteriosclerosis, Thrombosis and Vascular Biology 17, 595-599; Groenemeijer et al., 1997, Circulation 95, 2628-2635; Fisher et al., 1997, Atherosclerosis 135, 145-159; U.S. Pat. No. 5,658,729; Groenemeijer et al., *Circulation* 1997, 95:2628-2635; Gagne et al., *Clin. Genet.* 1999, 55(6):450-454). Correspondingly, in most studies this mutation seems to confer protection against CAD. The mechanism(s) behind these effects are not known.

SUMMARY OF THE INVENTION

One aspect of the invention involves the recognition of important advantages that may be obtained through therapeutic treatments comprising the administration of therapeutics derived from the LPL S447X protein and nucleic acid sequences encoding the LPL S447X protein. Such LPL S447X therapeutics may include LPL S447X peptides, nucleic acid sequences coding therefor, cells expressing such peptides or nucleic acids, and derivatives of such peptides, wherein the LPL S447X therapeutic ameliorates or treats disease when administered in prophylactically or therapeutically effective dosages. LPL S447X therapeutics of the invention include modifications, derivatives and analogs of LPL S447X peptides, and nucleic acids encoding such peptides. In some embodiments, the LPL S447X therapeutic of the invention may be a peptide having a sequence of amino acids corresponding to amino acids 1-446 of a naturally-occurring wild-type LPL peptide, as set out in FIG. 1 (SEQ ID NO: 1). A variety of naturally-occurring LPL peptides are known (Murthy V., Julien P., and Gagné C. 1996. Molecular pathobiology of the human lipoprotein lipase gene. Pharmacol. Ther. 70[2], 101-135). Alternative naturally-occurring LPL peptides may be identified by screening individual genomes, including non-human genomes, for sequences homologous to known LPL genes.

In alternative aspects, the invention provides for the use of an LPL S447X therapeutic, such as an LPL S447X protein or nucleic acid, for modulating LPL activity or LPL mass, for reducing plasma triglycerides and/or raising HDL-cholesterol, altering plasma lipid levels, or to treat an LPL-responsive condition in a patient. The invention also provides pharmaceutical compositions for such uses. Examples of LPL-responsive conditions that may be amenable to treatment in alternative embodiments include: complete LPL deficiency (including chronic (e.g. for life, chylomicronemia, hypoalphalipoproteinemia) and acute (e.g. pancreatitis, severe hyperlipidemia) whether genetic or acquired); partial LPL deficiency (including chronic and acute (e.g. pancreatitis, hyperlipidemia, in pregnancy, diabetes, alcoholism); hyperlipidemia which is not due to LPL deficiency (e.g. FH, FCH, Type II lipoproteinemia); hypertriglyceridemia (having a variety of causes); hypoalphalipoproteinemia (low HDL), low HDL-cholesterol levels; cardiovascular disease; coronary heart disease; coronary artery disease; atherosclerosis; angina pectoris; hypertension (high blood pressure); cerebrovascular disease; coronary restenosis; peripheral vascular disease; diabetes (hypertriglyceridemia and other related symptoms in diabetes and insulin resistant states); cachexia (for example in cancer or when there is an altered LPL expression profile); and obesity.

In one aspect the invention relates to the use of an LPL S447X therapeutic selected from the group consisting of:
a) an LPL S447X protein wherein the amino acid sequence of the LPL S447X protein comprises a contiguous segment having at least 90% sequence identity to SEQ ID NO:3 when optimally aligned, and wherein the LPL S447X protein lacks amino acids corresponding to amino acids 447 and 448 of SEQ ID NO:3 when optimally aligned; and,
b) an LPL S447X nucleic acid encoding the LPL S447X protein.

In some embodiments, the LPL S447X protein may have an LPL activity or other therapeutic property equal to or greater than a wild-type LPL, such as the LPL of SEQ ID NO:3

In one aspect, the invention relates to the use in gene therapy of an LPL S447X nucleic acid encoding the LPL S447X protein. The LPL S447X nucleic acid may be delivered by a therapeutically acceptable gene therapy vector to treat LPL-responsive conditions, such as the conditions set out above. The gene therapy vector may for example be an adeno-associated vector (AAV). Such a vector may comprise for example: a 5' inverted terminal repeat (ITR); a promoter, such as a CMV enhancer-promoter with a muscle specific enhancer; an intron; a 3'-untranslated region (3'-UTR); a polyadenylation signal, such as an SV40 polyadenylation signal; and a 3'-ITR.

BRIEF DESCRIPTION OF THE DRAWINGS

FIG. 1 is a listing of the amino acid sequence of LPL S447X, showing amino acids designated 1 through 446 herein (SEQ ID NO:1). The Figure reproduces information available from Genbank Accession NP_000228 for a *Homo sapiens* lipoprotein lipase precursor, version NP_000228.1, GI:4557727, incorporated herein by reference (Wion, et al., Science 235 (4796), 1638-1641 (1987); Sparkes et al., Genomics 1 (2), 138-144 (1987); Maffei et al., Cytogenet. Cell Genet. 63 (1), 45-46 (1993); Zechner, Curr. Opin. Lipidol. 8 (2), 77-88 (1997); Fisher et al., Atherosclerosis 135 (2), 145-159 (1997); and Beisiegel, Eur. Heart J. 19, A20-A23 (1998); Groenemeijer et al., *Circulation* 1997, 95:2628-2635; Gagné et al., *Clin. Genet.* 1999, 55(6):450-454).

FIG. 2 is a listing of the amino acid sequence of a mature wild-type LPL peptide, showing amino acids designated 1 through 448 herein (SEQ ID NO:2). The Figure reproduces information available from Genbank Accession NP_000228.

FIG. 3 is a listing of the amino acid sequence of a pre-LPL peptide, showing a protein having a signal peptide at amino acids 1 through 27, prior to the mature LPL peptide sequence (SEQ ID NO:3). The Figure reproduces information available from Genbank Accession NP_000228.

FIG. 4 is a listing of the sequence of an LPL mRNA, in which a signal peptide is encoded by nucleotides 175 through 255, and the mature peptide is encoded by nucleotides 256 through 1599 (SEQ ID NO:4). The Figure reproduces information available from Genbank Accession NM_000237 for a *Homo sapiens* lipoprotein lipase (LPL) mRNA, version NM_000237.1, GI:4557726, incorporated herein by reference (Wion, et al., Science 235 (4796), 1638-1641 (1987); Sparkes et al., Genomics 1 (2), 138-144 (1987); Maffei et al., Cytogenet. Cell Genet. 63 (1), 45-46 (1993); Zechner, Curr. Opin. Lipidol. 8 (2), 77-88 (1997); Fisher et al., Atherosclerosis 135 (2), 145-159 (1997); and Beisiegel, Eur. Heart J. 19, A20-A23 (1998)).

DETAILED DESCRIPTION OF THE INVENTION

In some embodiments, the LPL S447X therapeutic of the invention may include substantially purified compounds such as peptide fragments, modified peptide fragments, analogues or pharmacologically acceptable salts of LPL having amino acids 447-448 truncated from the carboxy terminal of a wild-type LPL, such compounds are collectively referred to herein as LPL S447X peptides. LPL S447X peptides may include homologs of the wild-type mature LPL sequence from amino acids 1 through 446, including homologs from species other than *homo sapiens* (which may have veterinary applications). LPL S447X peptides may include naturally occurring isoforms or genetic variants of wild type LPL. LPL polypeptides may also include polypeptides having substantial sequence similarity to wild type LPL amino acids 1 through 446, such as 90%, 95% or 99% sequence identity to a corresponding portion of the wild-type LPL 1-446 sequence, the corresponding portion of wild-type LPL being any contiguous sequence of any length, such as 10, 20, 30, 40, 50 or more amino acids. In some embodiments, such proteins may have LPL activity, or another LPL-like property, equal to or greater than wild type LPL. In some embodiments, chemically similar amino acids may be substituted for amino acids in the wild-type LPL sequence (to provide conservative amino acid substitutions). Amino acid substitutions that reduce LPL activity, of which more than 50 have been disclosed, such as the substitution of a Ser residue for Asn at position 291 (Asn291Ser), the substitution of Asn for Asp at position 9 (Asp9Asn), the substitution of Glu for Gly at position 188 (Gly188Glu, see Monsalve et al., *J. Clin. Invest.* 1990, 86(3):728-734) or Asp250Asn (Ma et al., Genomics. 1992, 13:649-653) may be avoided in preferred embodiments.

Two nucleic acid or protein sequences are considered substantially identical if, when optimally aligned, they share at least about 70% sequence identity. In alternative embodiments, sequence identity may for example be at least 75%, at least 90% or at least 95%. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J.*

Mol. Biol. 48:443, the search for similarity method of Pearson and Lipman, 1988, Proc. Natl. Acad. Sci. USA 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence alignment may also be carried out using the BLAST algorithm, described in Altschul et al., 1990, J. Mol. Biol. 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST programs may use as defaults a word length (W) of 11, the BLOSUM62 scoring matrix (Henikoff and Henikoff, 1992, Proc. Natl. Acad. Sci. USA 89: 10915-10919) alignments (B) of 50, expectation (E) of 10 (which may be changed in alternative embodiments to 1 or 0.1 or 0.01 or 0.001 or 0.0001; although E values much higher than 0.1 may not identify functionally similar sequences, it is useful to examine hits with lower significance, E values between 0.1 and 10, for short regions of similarity), M=5, N=4, for nucleic acids a comparison of both strands. For protein comparisons, BLASTP may be used with defaults as follows: G=11 (cost to open a gap); E=1 (cost to extend a gap); E=10 (expectation value, at this setting, 10 hits with scores equal to or better than the defined alignment score, S, are expected to occur by chance in a database of the same size as the one being searched; the E value can be increased or decreased to alter the stringency of the search.); and W=3 (word size, default is 11 for BLASTN, 3 for other blast programs).

The BLOSUM matrix assigns a probability score for each position in an alignment that is based on the frequency with which that substitution is known to occur among consensus blocks within related proteins. The BLOSUM62 (gap existence cost=11; per residue gap cost=1; lambda ratio=0.85) substitution matrix is used by default in BLAST 2.0. A variety of other matrices may be used as alternatives to BLOSUM62, including: PAM30 (9, 1, 0.87); PAM70 (10, 1, 0.87) BLOSUM80 (10, 1, 0.87); BLOSUM62 (11, 1, 0.82) and BLOSUM45 (14, 2, 0.87). One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

It is well known in the art that some modifications and changes can be made in the structure of a polypeptide without substantially altering the biological function of that peptide, to obtain a biologically equivalent polypeptide. In one aspect of the invention, LPL S447X therapeutics may include peptides that differ from a portion of the wild-type LPL sequence by conservative amino acid substitutions. As used herein, the term "conserved amino acid substitutions" refers to the substitution of one amino acid for another at a given location in the peptide, where the substitution can be made without loss of function. In making such changes, substitutions of like amino acid residues can be made, for example, on the basis of relative similarity of side-chain substituents, for example, their size, charge, hydrophobicity, hydrophilicity, and the like, and such substitutions may be assayed for their effect on the function of the peptide by routine testing.

In some embodiments, conserved amino acid substitutions may be made where an amino acid residue is substituted for another having a similar hydrophilicity value (e.g., within a value of plus or minus 2.0), where the following hydrophilicity values are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gin, Tyr.

The invention provides pharmaceutical compositions containing LPL S447X therapeutics. In some embodiments, such compositions may include a LPL S447X therapeutic in an effective amount, sufficient to provide a desired therapeutic or prophylactic effect, and a pharmaceutically acceptable carrier or excipient. An "effective amount" includes a therapeutically effective amount or a prophylactically effective amount.

A "therapeutically effective amount" refers to an amount effective, at dosages and for periods of time necessary, to achieve the desired therapeutic result, such as alteration of parameters in lipid metabolism, such as elevation of LPL activity, elevation of HDL-cholesterol or reduction of triglyceride levels. A therapeutically effective amount of LPL S447X therapeutic may vary according to factors such as the disease state, age, sex, and weight of the individual, and the ability of the LPL S447X therapeutic to elicit a desired response in the individual. Dosage regimens may be adjusted to provide the optimum therapeutic response. A therapeutically effective amount is also typically one in which any toxic or detrimental effects of the LPL S447X therapeutic are outweighed by the therapeutically beneficial effects.

A "prophylactically effective amount" refers to an amount effective, at dosages and for periods of time necessary, to achieve the desired prophylactic result, such as preventing or inhibiting various conditions, including LPL responsive conditions, such as coronary heart disease, cardiovascular disease, coronary artery disease, high triglycerides and/or low HDL. A prophylactic dose may be used in subjects prior to or at an earlier stage of disease, and a prophylactically effective amount may be more or less than a therapeutically effective amount in some cases.

In particular embodiments, a range for therapeutically or prophylactically effective amounts of LPL S447X therapeutic may be 0.01 nM-0.1M, 0.1 nM-0.1M, 0.1 nM-0.05M, 0.05 nM-15 µM or 0.01 nM-10 µM. It is to be noted that dosage values may vary with the severity of the condition to be alleviated. For any particular subject, specific dosage regimens may be adjusted over time according to the individual need and the professional judgement of the person administering or supervising the administration of the compositions. Dosage ranges set forth herein are exemplary only and do not limit the dosage ranges that may be selected by medical practitioners.

For gene therapy vectors, the dosage to be administered may depend to a large extent on the condition and size of the subject being treated as well as the therapeutic formulation, frequency of treatment and the route of administration. Regimens for continuing therapy, including dose, formulation, and frequency may be guided by the initial response and clinical judgment. The parenteral route of injection into the interstitial space of tissue may be preferred, although other parenteral routes, such as inhalation of an aerosol formulation, may be required in specific administration. In some protocols, a formulation comprising the gene and gene delivery system in an aqueous carrier is injected into tissue in appropriate amounts. The tissue target may be specific, for example the muscle or liver tissue, or it may be a combination of several tissues, for example the muscle and liver tissues. Exemplary tissue targets may include liver, skeletal muscle, heart muscle, adipose deposits, kidney, lung, vascular endothelium, epithelial and/or hematopoietic cells.

The amount of active compound in the compositions of the invention may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It may be advantageous to formulate parenteral compositions in dosage unit form for ease of administration and uniformity of dosage. "Dosage unit form" as used herein refers to physically discrete units suited as unitary dosages for subjects to be treated; each unit containing a predetermined quantity of active compound calculated to produce the desired therapeutic effect in association with the required pharmaceutical carrier. The specification for the dosage unit forms of the invention may be dictated by the unique characteristics of the active compound and the particular therapeutic effect to be achieved, and by the limitations inherent in the art of compounding such an active compound for the treatment of a condition in individuals.

As used herein "pharmaceutically acceptable carrier" or "exipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated.

Supplementary active compounds can also be incorporated into the pharmaceutical compositions of the invention. For example, ApoCil (in nucleic acid or protein form) may in some embodiments act as a co-activator of an LPL S447X therapeutic. Alternative active compounds may include compounds that augment the properties or action of an LPL S447X therapeutic. In some embodiments the LPL S447X therapeutic may be co-administered with a therapeutic, such as insulin, for treating an alternative condition, such as diabetes. In some embodiments, immune system modulators, such as cyclosporin, may be co-administered with the LPL S447X therapeutic, for example to ameliorate an immune response to the LPL S447X therapeutic. In assessing the risk of an immune response against an LPL S447X therapeutic, an analysis of the LPL gene of a patient may be carried out to characterize the patient's natural LPL. Guidance on co-administration of additional therapeutics may for example be found in the Compendium of Pharmaceutical and Specialties (CPS) of the Canadian Pharmacists Association.

Pharmaceutical compositions are typically sterile and stable under the conditions of manufacture and storage. Pharmaceutical compositions may be formulated as a solution, microemulsion, liposome, or other ordered structure suitable to accommodate high drug concentration. The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. The LPL S447X therapeutic may be administered in a time or controlled release formulation, for example in a composition which includes a slow release polymer or other carriers that will protect the compound against rapid release, including implants and microencapsulated delivery systems. Biodegradable, biocompatible polymers may for example be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound in the required amount in an appropriate solvent with one or a combination of ingredients enumerated herein, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, an LPL S447X therapeutic may be formulated with one or more additional compounds that enhance the solubility of the LPL S447X therapeutic.

LPL S447X therapeutic compounds of the invention may include derivatives, such as C-terminal hydroxymethyl derivatives, 0-modified derivatives (e.g., C-terminal hydroxymethyl benzyl ether), and N-terminally modified derivatives including substituted amides such as alkylamides and hydrazides.

Within an LPL S447X peptide of the invention, a peptidic structure maybe coupled directly or indirectly to a modifying group. The term "modifying group" is intended to include structures that are directly attached to the peptidic structure (e.g., by covalent coupling), as well as those that are indirectly attached to the peptidic structure (e.g., by a stable non-covalent association or by covalent coupling to additional amino acid residues, or mimetics, analogues or derivatives thereof, which may flank the MCP-3 core peptidic structure). For example, the modifying group can be coupled to the amino-terminus or carboxy-terminus of an LPL S447X peptidic structure, or to a peptidic or peptidomimetic region flanking the core domain. Alternatively, the modifying group can be coupled to a side chain of an amino acid residue of the LPL S447X peptide, or to a peptidic or peptido-mimetic region flanking the core domain (e.g., through the epsilon amino group of a lysyl residue(s), through the carboxyl group of an aspartic acid residue(s) or a glutamic acid residue(s), through a hydroxy group of a tyrosyl residue(s), a serine residue(s) or a threonine residue(s) or other suitable reactive group on an amino acid side chain). Modifying groups covalently coupled to the peptidic structure can be attached by means and using methods well known in the art for linking chemical structures, including, for example, amide, alkylamino, carbamate or urea bonds.

In some embodiments, the modifying group may comprise a cyclic, heterocyclic or polycyclic group. The term "cyclic group", as used herein, includes cyclic saturated or unsaturated (i.e., aromatic) group having from 3 to 10, 4 to 8, or 5 to 7 carbon atoms. Exemplary cyclic groups include cyclopropyl, cyclobutyl, cyclopentyl, cyclohexyl, and cyclooctyl. Cyclic groups may be unsubstituted or substituted at one or more ring positions. A cyclic group may for example be substituted with halogens, alkyls, cycloalkyls, alkenyls, alkynyls, aryls, heterocycles, hydroxyls, aminos, nitros, thiols amines, imines, amides, phosphonates, phosphines, carbonyls, carboxyls, silyls, ethers, thioethers, sulfonyls, sulfonates, selenoethers, ketones, aldehydes, esters, —$CF_3$, —CN.

The term "heterocyclic group" includes cyclic saturated, unsaturated and aromatic groups having from 3 to 10, 4 to 8, or 5 to 7 carbon atoms, wherein the ring structure includes about one or more heteroatoms. Heterocyclic groups include pyrrolidine, oxolane, thiolane, imidazole, oxazole, piperidine, piperazine, morpholine. The heterocyclic ring may be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, —CN. Heterocycles may also be bridged or fused to other cyclic groups as described below.

The term "polycyclic group" as used herein is intended to refer to two or more saturated, unsaturated or aromatic cyclic rings in which two or more carbons are common to two adjoining rings, so that the rings are "fused rings". Rings that are joined through non-adjacent atoms are termed "bridged" rings. Each of the rings of the polycyclic group may be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —$CF_3$, or —CN.

The term "alkyl" refers to the radical of saturated aliphatic groups, including straight chain alkyl groups, branched-chain alkyl groups, cycloalkyl (alicyclic) groups, alkyl substituted cycioalkyl groups, and cycloalkyl substituted alkyl groups. In some embodiments, a straight chain or branched chain alkyl has 20 or fewer carbon atoms in its backbone ($C_1$-$C_{20}$ for straight chain, $C_3$-$C_{20}$ for branched chain), or 10 or fewer carbon atoms. In some embodiments, cycloalkyls may have from 4-10 carbon atoms in their ring structure, such as 5, 6 or 7 carbon rings. Unless the number of carbons is otherwise specified, "lower alkyl" as used herein means an alkyl group, as defined above, having from one to ten carbon atoms in its backbone structure. Likewise, "lower alkenyl" and "lower alkynyl" have chain lengths of ten or less carbons.

The term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group. Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkyloxycarbonyl", as used herein, refers to the group —C(O)—O-alkyl, and the term "aryloxycarbonyl" refers to —C(O)—O-aryl. The term "acyloxy" refers to —O—C(O)—$R_7$, in which $R_7$ is alkyl, alkenyl, alkynyl, aryl, aralkyl or heterocyclyl.

The term "amino", as used herein, refers to —N($R_\alpha$)($R_\beta$), in which $R_\alpha$ and $R_\beta$ are each independently hydrogen, alkyl, alkyenyl, alkynyl, aralkyl, aryl, or in which $R_\alpha$ and $R_\beta$ together with the nitrogen atom to which they are attached form a ring having 4-8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N($R_8$)($R_9$), in which $R_8$ and $R_9$ are as defined above. The term "acylamino" refers to —N($R'_8$)C(O)—$R_7$, in which $R_7$ is as defined above and $R'_8$ is alkyl.

As used herein, the term "nitro" means —$NO_2$; the term "halogen" designates —F, —Cl, —Br or —I; the term "sulfhydryl" means —SH; and the term "hydroxyl" means —OH.

The term "aryl" as used herein includes 5-, 6-and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —$CF_3$, —CN, or the like. Aryl groups can also be part of a polycyclic group. For example, aryl groups include fused aromatic moieties such as naphthyl, anthracenyl, quinolyl, indolyl, and the like.

Modifying groups may include groups comprising biotinyl structures, fluorescein-containing groups, a diethylene-triaminepentaacetyl group, a (–)-menthoxyacetyl group, a N-acetylneuraminyl group, a cholyl structure or an iminiobiotinyl group. An LPL S447X peptide may be modified at its carboxy terminus with a cholyl group according to methods known in the art (for example see: Wess, G. et al. (1993) Tetrahedron Letters, 34:817-822; Wess, G. et al. (1992) Tetrahedron Letters 33:195-198; and Kramer, W. et al. (1992) J. Biol. Chem. 267:18598-18604). Cholyl derivatives and analogues may also be used as modifying groups, such as Aic (3-(O-aminoethyl-iso)-cholyl), which has a free amino group that can be used to further modify the LPL S447X peptide. A modifying group may be a "biotinyl structure", which includes biotinyl groups and analogues and derivatives thereof (such as a 2-iminobiotinyl group). In another embodiment, the modifying group may comprise a "fluorescein-containing group", such as a group derived from reacting an LPL S447X peptide with 5-(and 6-)-carboxyfluorescein, succinimidyl ester or fluorescein isothiocyanate. In various other embodiments, the modifying group(s) may comprise an N-acetylneuraminyl group, a trans-4-cotininecarboxyl group, a 2-imino-1-imidazolidineacetyl group, an (S)-(–)-indoline-2-carboxyl group, a (–)-menthoxyacetyl group, a 2-norbornaneacetyl group, a gamma-oxo-5-acenaphthenebutyryl, a (–)-2-oxo-4-thiazolidinecarboxyl group, a tetrahydro-3-furoyl group, a 2-iminobiotinyl group, a diethylenetriaminepentaacetyl group, a 4-morpholinecarbonyl group, a 2-thiopheneacetyl group or a 2-thiophenesulfonyl group.

An LPL S447X therapeutic of the invention may be further modified to alter the specific properties of the compound while retaining the desired functionality of the compound. For example, in one embodiment, the compound may be modified to alter a pharmacokinetic property of the compound, such as in vivo stability or half-life. The compound may be modified to label the compound with a detectable substance. The compound may be modified to couple the compound to an additional therapeutic moiety. To further chemically modify the compound, such as to alter its pharmacokinetic properties, reactive groups can be derivatized. Potential C-terminal modifications include those which reduce the ability of the compound to act as a substrate for carboxypeptidases. Examples of C-terminal modifiers include an amide group, an ethylamide group and various non-natural amino acids, such as D-amino acids and beta-alanine. Alternatively, when the modifying group is attached to the carboxy-terminal end of the aggregation core domain, the amino-terminal end of the compound may be further modified, for example, to reduce the ability of the compound to act as a substrate for aminopeptidases.

An LPL S447X therapeutic can be further modified to label the compound by reacting the compound with a detectable substance. Suitable detectable substances include various enzymes, prosthetic groups, fluorescent materials, luminescent materials and radioactive materials. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{14}C$, $^{123}I$, $^{124}I$, $^{125}I$, $^{131}I$, $^{99}Tc$, $^{35}S$ or $^3H$. An LPL S447X therapeutic may be radioactively labelled with $^{14}C$, either by incorporation of $^{14}C$ into the modifying group or one or more amino acid structures in the compound. Labelled LPL S447X therapeutics may be used to assess the in vivo pharmacokinetics of the compounds, as well as to detect disease progression or propensity of a subject to develop a disease, for example for diagnostic purposes. Tissue distribution of LPL S447X therapeutics can be detected using a labeled LPL S447X therapeutic either in vivo or in an in vitro sample derived from a subject. For use as an in vivo diagnostic agent, an LPL S447X therapeutic of the invention may for example be labelled with radioactive technetium or iodine. A modifying group can be chosen that provides a site at which a chelation group for the label can be introduced, such as an Aic derivative of cholic acid, which has a free amino group. For example, a phenylalanine residue within the LPL S447X peptide sequence may be substituted with radioactive iodotyrosyl. Any of the various isotopes of radioactive iodine may be incorporated to create a diagnostic agent. $^{123}I$ (half-life=13.2 hours) may be used for whole body scintography, $^{124}I$ (half life=4 days) may be used for positron emission tomography (PET), $^{125}I$ (half life=60 days) may be used for metabolic turnover studies and $^{131}I$ (half life=8 days) may be used for whole body counting and delayed low resolution imaging studies.

In an alternative chemical modification, an LPL S447X therapeutic of the invention may be prepared in a "prodrug" form, wherein the compound itself does not act as a therapeutic, but rather is capable of being transformed, upon metabolism in vivo, into an LPL S447X therapeutic as defined herein. For example, in this type of compound, the modifying group can be present in a prodrug form that is capable of being converted upon metabolism into the form of an active LPL S447X therapeutic. Such a prodrug form of a modifying group is referred to herein as a "secondary modifying group." A variety of strategies are known in the art for preparing peptide prodrugs that limit metabolism in order to optimize delivery of the active form of the peptide-based drug (see e.g., Moss, J. (1995) in Peptide-Based Drug Design: Controlling Transport and Metabolism, Taylor, M. D. and Amidon, G. L. (eds), Chapter 18).

LPL S447X peptide analogues of the invention may be prepared by standard techniques known in the art. LPL S447X peptide analogues may be composed, at least in part, of a peptide synthesized using standard techniques (such as those described in Bodansky, M. Principles of Peptide Synthesis, Springer Verlag, Berlin (1993); Grant, G. A. (ed.). Synthetic Peptides: A User's Guide, W. H. Freeman and Company, New York (1992); or Clark-Lewis, I., Dewald, B., Loetscher, M., Moser, B., and Baggiolini, M., (1994) J. Biol. Chem., 269, 16075-16081). Automated peptide synthesizers are commercially available (e.g., Advanced ChemTech Model 396; Milligen/Biosearch 9600). Peptides may be assayed for activity in accordance with standard methods. Peptides may be purified by HPLC and analyzed by mass spectrometry. Peptides may be dimerized via a disulfide bridge formed by gentle oxidation of the cysteines using 10% DMSO in water. Following HPLC purification dimer formation may be verified, by mass spectrometry. One or more modifying groups may be attached to an LPL S447X peptide by standard methods, for example using methods for reaction through an amino group (e.g., the alpha-amino group at the amino-terminus of a peptide), a carboxyl group (e.g., at the carboxy terminus of a peptide), a hydroxyl group (e.g., on a tyrosine, serine or threonine residue) or other suitable reactive group on an amino acid side chain (see e.g., Greene, T. W. and Wuts, P. G. M. Protective Groups in Organic Synthesis, John Wiley and Sons, Inc., New York (1991)).

In another aspect of the invention, LPL S447X peptides may be prepared according to standard recombinant DNA techniques using a nucleic acid molecule encoding the peptide. A nucleotide sequence encoding the peptide of interest may be determined using the genetic code and an oligonucleotide molecule having this nucleotide sequence may be synthesized by standard DNA synthesis methods (e.g., using an automated DNA synthesizer). Alternatively, a DNA molecule encoding a peptide compound may be derived from the natural precursor protein gene or cDNA (e.g., using the polymerase chain reaction (PCR) and/or restriction enzyme digestion) according to standard molecular biology techniques. For example, the human wild type LPL cDNA fragment may be cloned by RT-PCR from human adipose tissue total RNA using the following 5' and 3' UTR primers respectively; 5'-ATA GAA TTC GGA TCC ATC GAT/GC TCC TCC AGA GGG ACG GCG CCC CG-3' (which introduces an EcoRI, BamHI and ClaI site 5' of the LPL coding sequence) and 5'-TAT GTC GAC TAG ATA TC/GCC GTT CTT TGT TCT GTA GAT TCG CCC-3' (introducing SalI, XbaI and EcoRV sites 3' of the LPL coding sequence). The LPL S447X cDNAs may be derived from the wild type human 1.6 kb LPL cDNA by site directed mutagenesis (which may be confirmed by sequencing, see Henderson et al., 1991, Journal of Clinical Investigation 87, 2005-2011; and, Zhang et al., 1996Biochimica et Biophysica Acta 1302, 159-166).

The invention also provides an isolated nucleic acid molecule comprising a nucleotide sequence encoding an LPL S447X peptide of the invention. The term "nucleic acid molecule" includes DNA molecules and RNA molecules which may be single-stranded or double-stranded. In alternative embodiments, the isolated nucleic acid encodes a peptide wherein one or more amino acids are altered or deleted.

To facilitate expression of a peptide compound in a host cell by standard recombinant DNA techniques, the isolated nucleic acid encoding the peptide may be incorporated into a recombinant expression vector. Accordingly, the invention also provides recombinant expression vectors comprising the nucleic acid molecules of the invention. As used herein, the term "vector" refers to a nucleic acid, protein, lipid or other molecule capable of transporting a nucleic acid to which it has been operatively linked. Vectors may include circular double stranded DNA plasmids and viral vectors. Certain vectors are capable of autonomous replication in a host cell into which they are introduced (such as bacterial vectors having a bacterial origin of replication and episomal mammalian vectors). Other vectors (such as non-episomal mammalian vectors) may be integrated into the genome of a host cell upon introduction into the host cell, and thereby may be replicated along with the host genome. Certain vectors may be capable of directing the expression of genes to which they are operatively linked.

In recombinant vectors of the invention, the nucleotide sequence encoding a peptide may be operatively linked to one or more regulatory sequences, selected on the basis of the host cells to be used for expression. The terms "operatively linked" or "operably" linked mean that the sequences encoding the peptide are linked to the regulatory sequence(s) in a manner that allows for expression of the peptide compound. The term "regulatory sequence" includes promoters, enhancers, polyadenylation signals and other expression control elements. Such regulatory sequences are described, for example, in Goeddel; Gene Expression Technology: Methods in Enzymology 185, Academic Press, San Diego, Calif. (1990) (incorporated herein by reference). Regulatory sequences include those that direct constitutive expression of a nucleotide sequence in many types of host cell, those that direct expression of the nucleotide sequence only in certain host cells (such as tissue-specific regulatory sequences) and those that direct expression in a regulatable manner (such as only in the presence of an inducing agent). The design of the expression vector may depend on such factors as the choice of the host cell to be transformed and the level of expression of peptide compound desired.

Recombinant expression vectors of the invention may be designed for expression of peptide compounds in prokaryotic or eukaryotic cells. For example, peptide compounds may be expressed in bacterial cells such as *E. coli*, insect cells (using baculovirus expression vectors) yeast cells or mammalian cells. Suitable host cells are discussed further in Goeddel, Gene Expression Technology: Methods in Enzymology 185, Academic Press, San Diego, Calif. (1990). Alternatively, the recombinant expression vector may be transcribed and translated in vitro, for example using T7 promoter regulatory sequences and T7 polymerase. Examples of vectors for expression in yeast *S. cerivisae* include pYepSec1 (Baldari et al., (1987) EMBO J. 6:229-234), pMFa (Kurjan and Herskowitz, (1982) Cell 30:933-943), pJRY88 (Schultz et al., (1987) Gene 54:113-123), and pYES2 (Invitrogen Corporation, San Diego, Calif.). Baculovirus vectors available for expression of proteins or peptides in cultured insect cells (e.g., Sf 9 cells) include the pAc series (Smith et al., (1983) Mol. Cell. Biol. 3:2156-2165) and the pVL series (Lucklow, V. A., and Summers, M. D., (1989) Virology 170:31-39). Examples of mammalian expression vectors include pCDM8 (Seed, B., (1987) Nature 329:840) and pMT2PC (Kaufman et al. (1987), EMBO J. 6:187-195). When used in mammalian cells, the expression vector's control functions are often provided by viral regulatory elements. For example, commonly used promoters are derived from polyoma, Adenovirus 2, cytomegalovirus and Simian Virus 40.

In addition to regulatory control sequences, recombinant expression vectors may contain additional nucleotide sequences, such as a selectable marker gene to identify host cells that have incorporated the vector. Selectable marker genes are well known in the art. To facilitate secretion of the peptide compound from a host cell, in particular mammalian host cells, the recombinant expression vector preferably encodes a signal sequence operatively linked to sequences encoding the amino-terminus of the peptide compound, such that upon expression, the peptide compound is synthesised with the signal sequence fused to its amino terminus. This signal sequence directs the peptide compound into the secretory pathway of the cell and is then cleaved, allowing for release of the mature peptide compound (i.e., the peptide compound without the signal sequence) from the host cell. Use of a signal sequence to facilitate secretion of proteins or peptides from mammalian host cells is well known in the art.

A recombinant expression vector comprising a nucleic acid encoding a peptide compound may be introduced into a host cell to produce the peptide compound in the host cell. Accordingly, the invention also provides host cells containing the recombinant expression vectors of the invention. The terms "host cell" and "recombinant host cell" are used interchangeably herein. Such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. A host cell may be any prokaryotic or eukaryotic cell. For example, a peptide compound may be expressed in bacterial cells such as E. coli, insect cells, yeast or mammalian cells. The peptide compound may be expressed in vivo in a subject to the subject by gene therapy (discussed further below).

Vector DNA can be introduced into prokaryotic or eukaryotic cells via conventional transformation or transfection techniques. The terms "transformation" and "transfection" refer to techniques for introducing foreign nucleic acid into a host cell, including calcium phosphate or calcium chloride co-precipitation, DEAE-dextran-mediated transfection, lipofection, electroporation, microinjection and viral-mediated transfection. Suitable methods for transforming or transfecting host cells can for example be found in Sambrook et al. (Molecular Cloning: A Laboratory Manual, 2nd Edition, Cold Spring Harbor Laboratory press (1989)), and other laboratory manuals. Methods for introducing DNA into mammalian cells in vivo are also known, and may be used to deliver the vector DNA of the invention to a subject for gene therapy.

For stable transfection of mammalian cells, it is known that, depending upon the expression vector and transfection technique used, only a small fraction of cells may integrate the foreign DNA into their genome. In order to identify and select these integrants, a gene that encodes a selectable marker (such as resistance to antibiotics) may be introduced into the host cells along with the gene of interest.

Preferred selectable markers include those that confer resistance to drugs, such as G418, hygromycin and methotrexate. Nucleic acids encoding a selectable marker may be introduced into a host cell on the same vector as that encoding the peptide compound or may be introduced on a separate vector. Cells stably transfected with the introduced nucleic acid may be identified by drug selection (cells that have incorporated the selectable marker gene will survive, while the other cells die).

A nucleic acid of the invention may be delivered to cells in vivo using methods such as direct injection of DNA, receptor-mediated DNA uptake, viral-mediated transfection or non-viral transfection and lipid based transfection, all of which may involve the use of gene therapy vectors. Direct injection has been used to introduce naked DNA into cells in vivo (see e.g., Acsadi et al. (1991) Nature 332:815-818; Wolff et al. (1990) Science 247:1465-1468). A delivery apparatus (e.g., a "gene gun") for injecting DNA into cells in vivo may be used. Such an apparatus may be commercially available (e.g., from BioRad). Naked DNA may also be introduced into cells by complexing the DNA to a cation, such as polylysine, which is coupled to a ligand for a cell-surface receptor (see for example Wu, G. and Wu, C. H. (1988) J. Biol. Chem. 263: 14621; Wilson el al. (1992) J. Biol. Chem. 267:963-967; and U.S. Pat. No. 5,166,320). Binding of the DNA-ligand complex to the receptor may facilitate uptake of the DNA by receptor-mediated endocytosis. A DNA-ligand complex linked to adenovirus capsids which disrupt endosomes, thereby releasing material into the cytoplasm, may be used to avoid degradation of the complex by intracellular lysosomes (see for example Curiel el al. (1991) Proc. Natl. Acad. Sci. USA 88:8850; Cristiano et al. (1993) Proc. Natl. Acad. Sci. USA 90:2122-2126).

Defective retroviruses are well characterized for use as gene therapy vectors (for a review see Miller, A. D. (1990) Blood 76:271). Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are well known to those skilled in the art. Examples of suitable packaging virus lines include .pψi.Crip, .pψi.Cre, .pψi.2 and .pψi.Am. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

For use as a gene therapy vector, the genome of an adenovirus may be manipulated so that it encodes and expresses a peptide compound of the invention, but is inactivated in terms of its ability to replicate in a normal lytic viral life cycle. See for example Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) Proc. Natl. Acad. Sci. USA 89:6482-6486), hepatocytes (Herz and Gerard (1993) Proc. Natl. Acad. Sci. USA 90:2812-2816) and muscle cells (Quantin el al. (1992) Proc. Natl. Acad. Sci. USA 89:2581-2584).

Adeno-associated virus (AAV) may be used as a gene therapy vector for delivery of DNA for gene therapy purposes. AAV is a naturally occurring defective virus that requires another virus, such as an adenovirus or a herpes virus, as a helper virus for efficient replication and a productive life cycle (Muzyczka et al. Curr. Topics in Micro. and Immunol. (1992) 158:97-129). AAV may be used to integrate DNA into non-dividing cells (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). An AAV vector such as that described in Tratschin et al. (1985) Mol. Cell. Biol. 5:3251-3260 may be used to introduce DNA into cells (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790). Lentiviral gene therapy vectors may also be adapted for use in the invention.

General methods for gene therapy are known in the art. See for example, U.S. Pat. No. 5,399,346 by Anderson et al. (incorporated herein by reference). A biocompatible capsule for delivering genetic material is described in PCT Publication WO 95/05452 by Baetge et al. Methods of gene transfer into hematopoietic cells have also previously been reported (see Clapp, D. W., et al., Blood 78: 1132-1139 (1991); Anderson, Science 288:627-9 (2000); and, Cavazzana-Calvo et al., Science 288:669-72 (2000), all of which are incorporated herein by reference).

Genetic LPL deficiency may be classified into three categories depending on the LPL protein characteristics. Type I hypertriglyceridemic patients have very low to absent LPL protein mass. Type II patients produce little pre-heparin LPL protein but the level increases following heparin treatment. In class Type III, there are large amounts of circulating pre-heparin protein with little change in levels after heparin challenge. Although the utility of this classification system is limited, with some compound heterozygote patients spanning two of these classes, clarification of the presence or absence of plasma LPL protein may be important for deciding which patients are most likely to tolerate gene transfer without an immune reaction to LPL S447X therapeutics, with the spectrum being from Type I patients, being the most likely to develop an immune reaction, to Type II patients, being the least likely to develop an immune reaction.

EXAMPLE 1

Administration of LPL S447X Protein by Gene Therapy

A mouse model of human LPL deficiency has been created by gene-targeting to inactivate the murine LPL gene. All homozygous (−/−) pups die within 48 hours after birth with massive chylomicronemia from suckling milk. In attempt to rescue the −/− pups, intramuscular delivery of recombinant adenovirus containing the wild type human LPL gene (Ad-LPL) alone did not result in significant increase of human LPL mass in post-heparin plasma and did not rescue the lethality of complete LPL deficiency.

Intramuscular delivery of an Ad-447 gene therapy vector to newborn pups resulted in the appearance of human LPL mass in high levels in post-heparin plasma. In a litter of 4 pups, 2 were injected with Ad-447 ($2\times10^8$ pfu in 100 μl PBS) to 4 sites (25 μl/site) in 4 limbs at the day of birth. Two days later heparin at 1000 u/kg was injected intraperitoneally and the pups were sacrificed by decapitation to collect about 10 to 20 μl post-heparin plasma for analysis. One front and one hind limb were harvested and homogenized at 100 mg/ml in extraction buffer. The Results are shown in Table 1.

TABLE 1

|  | Cont'l | Ad-447 |
| --- | --- | --- |
| LPL mass in post-heparin plasma: (ng/ml) | 61.9 | 5351.2 |
|  | 61.0 | 8992.6 |
| LPL activity in muscle homogenate: (mU/ml) | 43.2 | 215.6 |
|  | 35.8 | 119.7 |
| LPL mass in muscle homogenate: (ng/ml) | 29.5 | 1820.7 |
|  | 45.3 | 1478.7 |

These results show that intramuscular delivery of a LPL S447X therapeutic by adenoviral-mediated gene transfer resulted in significant increase of human LPL protein mass in post-heparin plasma. These results are indicative of the surprisingly advantageous results obtainable using the LPL S447X therapeutics of the invention, as compared to wild type LPL.

An adenovirus vector of the invention for gene therapy may for example be produced utilizing the Adeno-Quest™ kit available from Quantum Biotechnologies Inc. (Montreal, QC, Canada). In an example of this approach, cDNAs were cloned into the shuttle plasmid pQBI-AdCMV5, which contains the CMV5 promoter and enhancer and a globin poly A. The LPL cDNAs (wild type and S447X) were double digested with HindIII and XbaI and inserted into the BamHI site via blunt end ligation. The human LPL gene was inserted 1.5 map units (mu) downstream from the 5' end of the adenovirus genome and is followed by mu 9.4-15.5 of Ad5 allowing for homologous recombination. The shuttle vector and the right end of the ClaI-digested, E3-deleted fragment of the Ad5 genome were co-transfected in 293 cells by calcium-phosphate precipitation and overlaid with 0.8% agarose in DMEM/5% FBS. After plaque purification, a high expressing clone was selected and amplified. At day 9 and 14 plaques were screened in vitro for LPL activity. Two clones with the highest LPL activity were chosen, plaque purified a second time and amplified in 293A cell culture on 15 cm plates. Purification of high titer recombinant virus (~$3\times10^{10}$ pfu/ml) was performed by double rounds of CsCl density gradient ultracentrifugation. The purified virus stocks were dialysized against 4 changes of HEPES buffered saline (HBS, 20 mM Hepes, 150 mM NaCl, pH 7.3) with 10% glycerol over 16-18 hours and stored at −80° C. Titers of the viral stocks were determined by plaque assay using 293 cells as described above. The titer was calculated as plaque forming units per milliliter (pfu/ml) and was 1-$3\times10^{10}$ pfu/ml. Virus preparations were quantified by Lowry protein assay consistently revealed ~50 particles per pfu from all Ad-LPL and Ad-447 preparations.

EXAMPLE 2

A serotype 5 adenovirus containing a LPL S447X gene under the control of the CMV-promoter was developed (Ad-447 as described in Example 1), and its effect compared to the effects of a wildtype LPL containing adenovirus. The animal model employed was the +/−LPL knock-out mouse model (Coleman et al., 1995, The Journal of Biological Chemistry 270[21], 12518-12525).

Preliminary in vitro studies done in HepG2 cells indicated a dose response relationship for LPL activity for the Ad-447 virus of a similar magnitude to the adenovirus containing the wild type LPL. There was, however, a marked difference in the amount of LPL immunoreactive mass. LPL immunoreactive mass in Ad-447 treated cells, at an MOI of 50 which infects essentially 100% of the cells, was roughly 4-fold greater that that of Ad-LPL.

When the dose response relationship of the Ad-447 virus was evaluated in a small cohort of mice via intravenous injection, unexpected results were obtained. The level of LPL activity was not responsive to 2 fold increases of virus ($5 \times 10^8$, $1 \times 10^9$ or $2 \times 10^9$ pfu/mouse). The level of activity was similar to that seen in the cohort of mice given $5 \times 10^8$ pfu of Ad-LPL. However, the level of LPL protein seen in these mice was exceptionally high. Despite activity apparently starting to decrease at day 7, the immunoreactive mass continued to increase at all three doses to a level of approximately 35-40,000 ng/ml. The majority of this protein at day 7 was observed in pre-heparin plasma and the small variation in lipolytic activity indicated that it was largely in an inactive form. Approximately 5000 ng/ml was found exclusively in post-heparin plasma. Over a time course of 70 days, LPL activity levels in mice given Ad-447 followed those of Ad-LPL closely and returned to baseline levels between 6 and 10 weeks post-injection. However, LPL immunoreactive protein levels were significantly elevated in mice receiving either Ad-LPL or Ad-447 with levels in the Ad-447 cohort maintaining profoundly elevated levels over the wild type Ad-LPL group. TG levels were significantly reduced at all three doses of Ad-447 in a manner similar to $5 \times 10^8$ pfu Ad-LPL. Both total and HDL cholesterol were significantly reduced until day 14.

To demonstrate dose response, LPL+/− mice (n=5/group) were given either $5 \times 10^7$ or $5 \times 10^8$ pfu of either Ad-447 or Ad-LPL (a dose $5 \times 10^7$ pfu is equivalent to approximately $5 \times 10^9$ particles). At a dose of $5 \times 10^8$ pfu of either Ad-LPL or Ad-447 per mouse, there was a significant 2.7 fold increase in plasma LPL activity accompanied by a significant increase in LPL protein levels at day 5 post gene transfer. Corresponding TG, HDL-C and Total-C levels also dropped significantly. At this dose, the only significant difference between the adenovector containing the wild type LPL cDNA versus the Ad-447 was the plasma LPL protein level, which was elevated in the Ad-447 group. Although significantly elevated in both groups over baseline or control mice, post-heparin LPL protein levels were still most profoundly elevated in the Ad-447 group (p<0.03). The most provocative differences observed only at the lower dose were in TG and cholesterol measures. At 3 days post-gene transfer, TG levels were significantly decreased in both Ad-LPL and Ad-447 groups, indicating the efficacy of the transferred LPL in both groups of mice. However, there was a significant increase in both HDL-C and total-C only in the Ad-447 group (p<0.01 and p<0.03 respectively, as compared to baseline or Ad-LPL treatment). The magnitude of these alterations, when compared to baseline levels, indicate that the majority of the increase in total-C is within the HDL-C fraction. At this same dose in the Ad-LPL cohort, there was a slight decrease in both total-C and HDL-C with only the decrease in total-C achieving significance (p=0.04). This illustrates an increased HDL-C content after adenovirus-mediated gene transfer of the human LPL S447X gene in mice. A similar significant elevation of the HDL-C fraction was observed at day 7, resolving by day 14.

EXAMPLE 3

This example illustrates that LPL mass and activity is associated with the severity of ischaemia and angina pectoris, indicating that the S447X therapeutics of the present invention may be used to treat such conditions by elevating LPL mass or activity.

In this example, post-heparin levels of LPL activity and mass were measured in a large cohort of male CHD patients participating in the REGRESS study, a lipid lowering regression trial (Jukema et al., 1995, Circulation 91: 2528-2540). In addition the relationships between LPL activity and mass and severity of angina pectoris according to the NYHA classification and silent ischaemia on 24 hour ambulatory (A)ECG monitoring were assessed. The results indicated that patients in different LPL activity quartiles and mass had different severity of angina; a total of 47% of patients in the lowest LPL quartile reported class 3 or 4 angina. By contrast, only 29% in the highest activity quartile (p=0.002) had severe angina. These parameters were supported by AECG results; where the total ischaemic burden in the lowest LPL activity quartile was 36.5 (104.1) mm·min, versus 14.8 (38.8) mm·min in the highest quartile of LPL activity (p=0.001). LPL activity levels were strongly correlated with LPL-mass (r=0.70; p<0.0001). A significant association between the LPL-protein mass and NYHA class (p=0.012) was also demonstrated. These results demonstrate a significant relationship between LPL mass and activity and severity of ischaemia as defined by angina class and AECG, indicating that LPL S447X therapeutics that adjust effective LPL mass or activity may be used to treat ischaemia and angina pectoris.

EXAMPLE 4

This example illustrates that LPL S447X protein is associated with protection against coronary heart disease, indicating that the S447X therapeutics of the present invention may be used to treat this condition. A total of 1114 men and 1144 women were randomly ascertained from the Framingham Offspring Study (FOS) for the presence of the LPL S447X gene. Carrier frequency of the LPL S447X allele was 17%, and in men carrier status was associated with higher total cholesterol (TC) (Δ=6.2 mg/dl, p=0.03), higher HDL-C (Δ=2.3 mg/dl, p=0.01) and lower triglyceride (TG) levels (Δ=−19.4 mg/dl, p=0.02). Moreover, in men the LPL S447X allele conferred significant protection against CHD (odds ratio: 0.43; p=0.04).

EXAMPLE 5

This example demonstrates the utility of LPL S447X therapeutics in an alternative model of human disease. The animal model employed was the completely deficient (−/−) ApoE knock-out mouse model. The therapeutic effect of a serotype 5 adenovirus containing an LPL S447X gene under the control of the CMV-promoter (Ad-447 virus) was compared to the therapeutic effect of a wildtype LPL-containing adenovirus (Ad-LPL), as well as to a control alkaline phosphatase (AP) containing adenovirus (Ad-AP).

Intravenous tail vein injection of $5 \times 10^8$ pfu of Ad-447 or wild type Ad-LPL resulted in a large reduction of plasma TG levels and a large increase in both LPL activity and protein mass levels in post-heparin plasma, in comparison to control injected Ad-AP mice, revealing the surprising efficacy of LPL S447X therapeutics in alternative therapies involving modulation of LPL activity or mass.

TABLE 2

| | | Pre-heparin Plasma | | | Post-heparin Plasma | |
|---|---|---|---|---|---|---|
| Virus | N | TG (mg/dl) | HDL-C (mg/dl) | T-C (mg/dl) | LPL Activity (mU/ml) | LPL Mass (ng/ml) |
| Control | 2 | 34 ± 7 | 12 ± 1 | 192 ± 1 | 784 ± 222 | 13 ± 22 |
| Ad-447 | 1 | 0 | 14 | 178 | 1395 | 9810 |
| Ad-LPL | 2 | 5 ± 3 | 13 ± 4 | 178 ± 3 | 1335 ± 39 | 5511 ± 3447 |

Table 2 illustrates LPL and lipid measures 3 days after the administration of $5 \times 10^8$ pfu of Ad-LPL, Ad-447 or control Alkaline Phosphatase to ApoE deficient mice. In agreement with data obtained in heterozygous LPL deficient mice, plasma triglycerides were decreased while both LPL activity and protein mass levels were increased in mice receiving Ad-LPL or Ad-447, with Ad-447 providing comparatively greater TG reduction, increased LPL activity and very significant LPL mass enhancement.

An exemplary protocol for assaying the effect of intravenous and intramuscular delivery of an LPL S447X therapeutic in an animal disease model are as follows. A serotype 5 adenovirus containing an LPL S447X gene under the control of the CMV-promoter (Ad-447) may be compared to the effects of a wildtype LPL containing adenovirus, Ad-LPL. The animal model may be the +1-LPL knock-out mouse model (Coleman et al., 1995, The Journal of Biological Chemistry 270[21], 12518-12525). For example, a total dose of $5 \times 10^8$ pfu may be diluted into 120 ul with a sterile saline solution and divided into 4 equal parts. A volume of 30 ul may be injected directly into the tibialis anterior and the gastrocnemius of both legs of each mouse for a total dose of $5 \times 10^8$ pfu per mouse. Blood may be obtained at days 3 and 7 post-treatment and the muscle categories may be isolated 14 days post-treatment for tissue analysis.

Conclusion

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein.

What is claimed is:

1. A method of treating a lipoprotein lipase (LPL)-responsive hyperlipidemia in a subject, wherein the hyperlipidemia is associated with LPL or ApoE deficiency, comprising administering to the subject an amount of an LPL S447X therapeutic effective to lower triglycerides and to raise HDL-C, wherein the LPL S447X therapeutic comprises an LPL S447X nucleic acid in a viral gene therapy vector encoding an LPL S447X protein, wherein the gene therapy vector is an adenoviral vector or an adeno-associated viral vector.

2. The method of claim 1, wherein the
LPL S447X protein comprises a contiguous segment having at least 90% sequence identity to SEQ ID NO:3 when optimally aligned, and wherein the LPL S447X protein lacks amino acids corresponding to amino, acids 447 and 448 of SEQ ID NO:3 when optimally aligned.

3. The method of claim 1, wherein the LPL S447X protein has greater LPL activity than a wild type LPL of SEQ ID NO:3.

4. The method of claim 1, wherein the LPL S447X nucleic acid comprises a DNA coding sequence encoding an RNA having at least 90% sequence identity to nucleotides 256 through 1599 of SEQ ID NO:4.

5. The method of claim 1, wherein the LPL S447X nucleic acid comprises a DNA coding sequence that hybridizes under stringent conditions to nucleotides 256 through 1599 of SEQ ID NO:4.

6. The method of claim 2, wherein the contiguous segment has at least 95% sequence identity to SEQ ID NO:1.

7. The method of claim 1, wherein the subject is a human.

8. The method of claim 1, wherein the LPL S447X protein comprises a contiguous segment having at least 90% sequence identity to SEQ ID NO:3 when optimally aligned, and wherein the LPL S447X protein lacks amino acids corresponding to amino acids 447 and 448 of SEQ ID NO:3 when optimally aligned, wherein the LPL S447X protein has greater LPL activity than a wild type LPL of SEQ ID NO:3, wherein the LPL S447X nucleic acid comprises a DNA coding sequence encoding an RNA having at least 90% sequence identity to nucleotides 256 through 1599 of SEQ ID NO:4, wherein the LPL S447X nucleic acid comprises a DNA coding sequence that hybridizes under stringent conditions to nucleotides 256 through 1599 of SEQ ID NO:4, and wherein the subject is a human.

9. The method of claim 8, wherein the contiguous segment has at least 95% sequence identity to SEQ ID NO:1.

10. The method of claim 1, wherein the hyperlipidemia is associated with complete LPL deficiency.

11. The method of claim 8, wherein the hyperlipidemia is associated with complete LPL deficiency.

\* \* \* \* \*

SEQUENCE LISTING

```
<160> NUMBER OF SEQ ID NOS: 4

<210> SEQ ID NO 1
<211> LENGTH: 446
<212> TYPE: PRT
<213> ORGANISM: Homo sapiens

<400> SEQUENCE: 1

Ala Asp Gln Arg Arg Asp Phe Ile Asp Ile Glu Ser Lys Phe Ala Leu
1               5                   10                  15

Arg Thr Pro Glu Asp Thr Ala Glu Asp Thr Cys His Leu Ile Pro Gly
            20                  25                  30

Val Ala Glu Ser Val Ala Thr Cys His Phe Asn His Ser Ser Lys Thr
        35                  40                  45

Phe Met Val Ile His Gly Trp Thr Val Thr Gly Met Tyr Glu Ser Trp
    50                  55                  60

Val Pro Lys Leu Val Ala Ala Leu Tyr Lys Arg Glu Pro Asp Ser Asn
65                  70                  75                  80

Val Ile Val Val Asp Trp Leu Ser Arg Ala Gln Glu His Tyr Pro Val
                85                  90                  95

Ser Ala Gly Tyr Thr Lys Leu Val Gly Gln Asp Val Ala Arg Phe Ile
            100                 105                 110

Asn Trp Met Glu Glu Glu Phe Asn Tyr Pro Leu Asp Asn Val His Leu
        115                 120                 125

Leu Gly Tyr Ser Leu Gly Ala His Ala Ala Gly Ile Ala Gly Ser Leu
    130                 135                 140

Thr Asn Lys Lys Val Asn Arg Ile Thr Gly Leu Asp Pro Ala Gly Pro
145                 150                 155                 160

Asn Phe Glu Tyr Ala Glu Ala Pro Ser Arg Leu Ser Pro Asp Asp Ala
                165                 170                 175
```

-continued

```
Asp Phe Val Asp Val Leu His Thr Phe Thr Arg Gly Ser Pro Gly Arg
            180                 185                 190

Ser Ile Gly Ile Gln Lys Pro Val Gly His Val Asp Ile Tyr Pro Asn
        195                 200                 205

Gly Gly Thr Phe Gln Pro Gly Cys Asn Ile Gly Glu Ala Ile Arg Val
    210                 215                 220

Ile Ala Glu Arg Gly Leu Gly Asp Val Asp Gln Leu Val Lys Cys Ser
225                 230                 235                 240

His Glu Arg Ser Ile His Leu Phe Ile Asp Ser Leu Leu Asn Glu Glu
                245                 250                 255

Asn Pro Ser Lys Ala Tyr Arg Cys Ser Ser Lys Glu Ala Phe Glu Lys
            260                 265                 270

Gly Leu Cys Leu Ser Cys Arg Lys Asn Arg Cys Asn Asn Leu Gly Tyr
        275                 280                 285

Glu Ile Asn Lys Val Arg Ala Lys Arg Ser Ser Lys Met Tyr Leu Lys
    290                 295                 300

Thr Arg Ser Gln Met Pro Tyr Lys Val Phe His Tyr Gln Val Lys Ile
305                 310                 315                 320

His Phe Ser Gly Thr Glu Ser Glu Thr His Thr Asn Gln Ala Phe Glu
                325                 330                 335

Ile Ser Leu Tyr Gly Thr Val Ala Glu Ser Glu Asn Ile Pro Phe Thr
            340                 345                 350

Leu Pro Glu Val Ser Thr Asn Lys Thr Tyr Ser Phe Leu Ile Tyr Thr
        355                 360                 365

Glu Val Asp Ile Gly Glu Leu Leu Met Leu Lys Leu Lys Trp Lys Ser
    370                 375                 380

Asp Ser Tyr Phe Ser Trp Ser Asp Trp Trp Ser Ser Pro Gly Phe Ala
385                 390                 395                 400

Ile Gln Lys Ile Arg Val Lys Ala Gly Glu Thr Gln Lys Lys Val Ile
                405                 410                 415

Phe Cys Ser Arg Glu Lys Val Ser His Leu Gln Lys Gly Lys Ala Pro
            420                 425                 430

Ala Val Phe Val Lys Cys His Asp Lys Ser Leu Asn Lys Lys
        435                 440                 445

<210> SEQ ID NO 2
<211> LENGTH: 475
<212> TYPE: PRT
<213> ORGANISM: Homo sapiens

<400> SEQUENCE: 2

Met Glu Ser Lys Ala Leu Leu Val Leu Thr Leu Ala Val Trp Leu Gln
1               5                   10                  15

Ser Leu Thr Ala Ser Arg Gly Val Ala Ala Ala Asp Gln Arg Arg
            20                  25                  30

Asp Phe Ile Asp Ile Glu Ser Lys Phe Ala Leu Arg Thr Pro Glu Asp
            35                  40                  45

Thr Ala Glu Asp Thr Cys His Leu Ile Pro Gly Val Ala Glu Ser Val
        50                  55                  60

Ala Thr Cys His Phe Asn His Ser Ser Lys Thr Phe Met Val Ile His
65                  70                  75                  80

Gly Trp Thr Val Thr Gly Met Tyr Glu Ser Trp Val Pro Lys Leu Val
                85                  90                  95

Ala Ala Leu Tyr Lys Arg Glu Pro Asp Ser Asn Val Ile Val Val Asp
            100                 105                 110
```

Trp Leu Ser Arg Ala Gln Glu His Tyr Pro Val Ser Ala Gly Tyr Thr
            115                 120                 125

Lys Leu Val Gly Gln Asp Val Ala Arg Phe Ile Asn Trp Met Glu Glu
        130                 135                 140

Glu Phe Asn Tyr Pro Leu Asp Asn Val His Leu Leu Gly Tyr Ser Leu
145                 150                 155                 160

Gly Ala His Ala Ala Gly Ile Ala Gly Ser Leu Thr Asn Lys Lys Val
                165                 170                 175

Asn Arg Ile Thr Gly Leu Asp Pro Ala Gly Pro Asn Phe Glu Tyr Ala
            180                 185                 190

Glu Ala Pro Ser Arg Leu Ser Pro Asp Asp Ala Asp Phe Val Asp Val
        195                 200                 205

Leu His Thr Phe Thr Arg Gly Ser Pro Gly Arg Ser Ile Gly Ile Gln
            210                 215                 220

Lys Pro Val Gly His Val Asp Ile Tyr Pro Asn Gly Gly Thr Phe Gln
225                 230                 235                 240

Pro Gly Cys Asn Ile Gly Glu Ala Ile Arg Val Ile Ala Glu Arg Gly
                245                 250                 255

Leu Gly Asp Val Asp Gln Leu Val Lys Cys Ser His Glu Arg Ser Ile
            260                 265                 270

His Leu Phe Ile Asp Ser Leu Leu Asn Glu Glu Asn Pro Ser Lys Ala
        275                 280                 285

Tyr Arg Cys Ser Ser Lys Glu Ala Phe Glu Lys Gly Leu Cys Leu Ser
            290                 295                 300

Cys Arg Lys Asn Arg Cys Asn Asn Leu Gly Tyr Glu Ile Asn Lys Val
305                 310                 315                 320

Arg Ala Lys Arg Ser Ser Lys Met Tyr Leu Lys Thr Arg Ser Gln Met
                325                 330                 335

Pro Tyr Lys Val Phe His Tyr Gln Val Lys Ile His Phe Ser Gly Thr
            340                 345                 350

Glu Ser Glu Thr His Thr Asn Gln Ala Phe Glu Ile Ser Leu Tyr Gly
        355                 360                 365

Thr Val Ala Glu Ser Glu Asn Ile Pro Phe Thr Leu Pro Glu Val Ser
        370                 375                 380

Thr Asn Lys Thr Tyr Ser Phe Leu Ile Tyr Thr Glu Val Asp Ile Gly
385                 390                 395                 400

Glu Leu Leu Met Leu Lys Leu Lys Trp Lys Ser Asp Ser Tyr Phe Ser
                405                 410                 415

Trp Ser Asp Trp Trp Ser Ser Pro Gly Phe Ala Ile Gln Lys Ile Arg
            420                 425                 430

Val Lys Ala Gly Glu Thr Gln Lys Lys Val Ile Phe Cys Ser Arg Glu
        435                 440                 445

Lys Val Ser His Leu Gln Lys Gly Lys Ala Pro Ala Val Phe Val Lys
        450                 455                 460

Cys His Asp Lys Ser Leu Asn Lys Lys Ser Gly
465                 470                 475

<210> SEQ ID NO 3
<211> LENGTH: 448
<212> TYPE: PRT
<213> ORGANISM: Homo sapiens

<400> SEQUENCE: 3

Ala Asp Gln Arg Arg Asp Phe Ile Asp Ile Glu Ser Lys Phe Ala Leu

-continued

```
  1               5                    10                    15
Arg Thr Pro Glu Asp Thr Ala Glu Asp Thr Cys His Leu Ile Pro Gly
                 20                   25                   30

Val Ala Glu Ser Val Ala Thr Cys His Phe Asn His Ser Lys Thr
                 35                   40                  45

Phe Met Val Ile His Gly Trp Thr Val Thr Gly Met Tyr Glu Ser Trp
                 50                   55                   60

Val Pro Lys Leu Val Ala Ala Leu Tyr Lys Arg Glu Pro Asp Ser Asn
 65                  70                   75                   80

Val Ile Val Val Asp Trp Leu Ser Arg Ala Gln Glu His Tyr Pro Val
                     85                   90                   95

Ser Ala Gly Tyr Thr Lys Leu Val Gly Gln Asp Val Ala Arg Phe Ile
                100                  105                  110

Asn Trp Met Glu Glu Phe Asn Tyr Pro Leu Asp Asn Val His Leu
                115                  120                  125

Leu Gly Tyr Ser Leu Gly Ala His Ala Ala Gly Ile Ala Gly Ser Leu
                130                  135                  140

Thr Asn Lys Lys Val Asn Arg Ile Thr Gly Leu Asp Pro Ala Gly Pro
145                  150                  155                  160

Asn Phe Glu Tyr Ala Glu Ala Pro Ser Arg Leu Ser Pro Asp Asp Ala
                165                  170                  175

Asp Phe Val Asp Val Leu His Thr Phe Thr Arg Gly Ser Pro Gly Arg
                180                  185                  190

Ser Ile Gly Ile Gln Lys Pro Val Gly His Val Asp Ile Tyr Pro Asn
                195                  200                  205

Gly Gly Thr Phe Gln Pro Gly Cys Asn Ile Gly Glu Ala Ile Arg Val
                210                  215                  220

Ile Ala Glu Arg Gly Leu Gly Asp Val Asp Gln Leu Val Lys Cys Ser
225                  230                  235                  240

His Glu Arg Ser Ile His Leu Phe Ile Asp Ser Leu Leu Asn Glu Glu
                245                  250                  255

Asn Pro Ser Lys Ala Tyr Arg Cys Ser Ser Lys Glu Ala Phe Glu Lys
                260                  265                  270

Gly Leu Cys Leu Ser Cys Arg Lys Asn Arg Cys Asn Asn Leu Gly Tyr
                275                  280                  285

Glu Ile Asn Lys Val Arg Ala Lys Arg Ser Ser Lys Met Tyr Leu Lys
                290                  295                  300

Thr Arg Ser Gln Met Pro Tyr Lys Val Phe His Tyr Gln Val Lys Ile
305                  310                  315                  320

His Phe Ser Gly Thr Glu Ser Glu Thr His Thr Asn Gln Ala Phe Glu
                325                  330                  335

Ile Ser Leu Tyr Gly Thr Val Ala Glu Ser Glu Asn Ile Pro Phe Thr
                340                  345                  350

Leu Pro Glu Val Ser Thr Asn Lys Thr Tyr Ser Phe Leu Ile Tyr Thr
                355                  360                  365

Glu Val Asp Ile Gly Glu Leu Leu Met Leu Lys Leu Lys Trp Lys Ser
                370                  375                  380

Asp Ser Tyr Phe Ser Trp Ser Asp Trp Trp Ser Ser Pro Gly Phe Ala
385                  390                  395                  400

Ile Gln Lys Ile Arg Val Lys Ala Gly Glu Thr Gln Lys Lys Val Ile
                405                  410                  415

Phe Cys Ser Arg Glu Lys Val Ser His Leu Gln Lys Gly Lys Ala Pro
                420                  425                  430
```

Ala Val Phe Val Lys Cys His Asp Lys Ser Leu Asn Lys Lys Ser Gly
        435                 440                 445

<210> SEQ ID NO 4
<211> LENGTH: 3549
<212> TYPE: DNA
<213> ORGANISM: Homo sapiens

<400> SEQUENCE: 4

| | | | | | |
|---|---|---|---|---|---|
| ccnctcttcc | tcctcctcaa | gggaaagctg | cccacttcta | gctgccctgc | catcccattt | 60 |
| aaagggcgac | ttgctcagcg | ccaaaccgcg | gctccagccc | tctccagcct | ccggctcagc | 120 |
| cggctcatca | gtcggtccgc | gccttgcagc | tcctccagag | ggacgcgccc | cgagatggag | 180 |
| agcaaagccc | tgctcgtgct | gactctggcc | gtgtggctcc | agagtctgac | cgcctcccgc | 240 |
| ggaggggtgg | ccgccgccga | ccaaagaaga | gattttatcg | acatcgaaag | taaatttgcc | 300 |
| ctaaggaccc | ctgaagacac | agctgaggac | acttgccacc | tcattcccgg | agtagcagag | 360 |
| tccgtggcta | cctgtcattt | caatcacagc | agcaaaacct | tcatggtgat | ccatggctgg | 420 |
| acggtaacag | gaatgtatga | gagttgggtg | ccaaaacttg | tggccgccct | gtacaagaga | 480 |
| gaaccagact | ccaatgtcat | tgtggtggac | tggctgtcac | gggctcagga | gcattaccca | 540 |
| gtgtccgcgg | gctacaccaa | actggtggga | caggatgtgg | cccggtttat | caactggatg | 600 |
| gaggaggagt | ttaactaccc | tctggacaat | gtccatctct | tgggatacag | ccttggagcc | 660 |
| catgctgctg | gcattgcagg | aagtctgacc | aataagaaag | tcaacagaat | tactggcctc | 720 |
| gatccagctg | gacctaactt | tgagtatgca | gaagccccga | gtcgtctttc | tcctgatgat | 780 |
| gcagattttg | tagacgtctt | acacacattc | accagagggt | cccctggtcg | aagcattgga | 840 |
| atccagaaac | cagttgggca | tgttgacatt | tacccgaatg | gggtactttt | cagccagga | 900 |
| tgtaacattg | agaagctat | ccgcgtgatt | gcagagagag | acttggaga | tgtggaccag | 960 |
| ctagtgaagt | gctcccacga | gcgctccatt | catctcttca | tcgactctct | gttgaatgaa | 1020 |
| gaaaatccaa | gtaaggccta | caggtgcagt | tccaaggaag | cctttgagaa | agggctctgc | 1080 |
| ttgagttgta | gaaagaaccg | ctgcaacaat | ctgggctatg | agatcaataa | agtcagagcc | 1140 |
| aaaagaagca | gcaaaatgta | cctgaagact | cgttctcaga | tgcccctacaa | agtcttccat | 1200 |
| taccaagtaa | agattcattt | ttctgggact | gagagtgaaa | cccataccaa | tcaggcctt | 1260 |
| gagatttctc | tgtatggcac | cgtggccgag | agtgagaaca | tcccattcac | tctgcctgaa | 1320 |
| gtttccacaa | ataagaccta | ctccttccta | atttacacag | aggtagatat | tggagaacta | 1380 |
| ctcatgttga | agctcaaatg | gaagagtgat | tcatacttta | gctggtcaga | ctggtggagc | 1440 |
| agtcccggct | tcgccattca | gaagatcaga | gtaaaagcag | gagagactca | gaaaaggtg | 1500 |
| atcttctgtt | ctagggagaa | agtgtctcat | ttgcagaaag | gaaaggcacc | tgcggtattt | 1560 |
| gtgaaatgcc | atgacaagtc | tctgaataag | aagtcaggct | gaaactgggc | gaatctacag | 1620 |
| aacaaagaac | ggcatgtgaa | ttctgtgaag | aatgaagtgg | aggaagtaac | ttttacaaaa | 1680 |
| catacccagt | gtttggggtg | tttcaaaagt | ggattttcct | gaatattaat | cccagcccta | 1740 |
| cccttgttag | ttattttagg | agacagtctc | aagcactaaa | agtggctaa | ttcaatttat | 1800 |
| ggggtatagt | ggccaaatag | cacatcctcc | aacgttaaaa | gacagtggat | catgaaaagt | 1860 |
| gctgttttgt | cctttgagaa | agaaataatt | gtttgagcgc | agagtaaaat | aaggctcctt | 1920 |
| catgtggcgt | attgggccat | agcctataat | tggttagaac | ctcctatttt | aattggaatt | 1980 |
| ctggatcttt | cggactgagg | ccttctcaaa | ctttactcta | agtctccaag | aatacagaaa | 2040 |

```
                                    -continued
atgcttttcc gcggcacgaa tcagactcat ctacacagca gtatgaatga tgttttagaa  2100
tgattccctc ttgctattgg aatgtggtcc agacgtcaac caggaacatg taacttggag  2160
agggacgaag aaagggtctg ataaacacag aggttttaaa cagtccctac cattggcctg  2220
catcatgaca aagttacaaa ttcaaggaga tataaaatct agatcaatta attcttaata  2280
ggctttatcg tttattgctt aatccctctc tcccccttct tttttgtctc aagattatat  2340
tataataatg ttctctgggt aggtgttgaa aatgagcctg taatcctcag ctgacacata  2400
atttgaatgg tgcagaaaaa aaaaagatac cgtaattta ttattagatt ctccaaatga  2460
ttttcatcaa tttaaaatca ttcaatatct gacagttact cttcagtttt aggcttacct  2520
tggtcatgct tcagttgtac ttccagtgcg tctcttttgt tcctggcttt gacatgaaaa  2580
gataggtttg agttcaaatt ttgcattgtg tgagcttcta cagattttag acaaggaccg  2640
tttttactaa gtaaagggt ggagaggttc ctggggtgga ttcctaagca gtgcttgtaa  2700
accatcgcgt gcaatgagcc agatggagta ccatgagggt tgttatttgt tgttttttaac  2760
aactaatcaa gagtgagtga acaactattt ataaactaga tctcctattt ttcagaatgc  2820
tcttctacgt ataaatatga aatgataaag atgtcaaata tctcagaggc tatagctggg  2880
aacccgactg tgaaagtatg tgatatctga acacatacta gaaagctctg catgtgtgtt  2940
gtccttcagc ataattcgga agggaaaaca gtcgatcaag ggatgtattg gaacatgtcg  3000
gagtagaaat tgttcctgat gtgccagaac ttcgaccctt tctctgagag agatgatcgt  3060
gcctataaat agtaggacca atgttgtgat taacatcatc aggcttggaa tgaattctct  3120
ctaaaaataa aatgatgtat gatttgttgt tggcatcccc tttattaatt cattaaattt  3180
ctggatttgg gttgtgaccc agggtgcatt aacttaaaag attcactaaa gcagcacata  3240
gcactgggaa ctctggctcc gaaaaacttt gttatatata tcaaggatgt tctggctta   3300
cattttattt attagctgta aatacatgtg tggatgtgta aatggagctt gtacatattg  3360
gaaaggtcat tgtggctatc tgcatttata aatgtgtggt gctaactgta tgtgtcttta  3420
tcagtgatgg tctcacagag ccaactcact cttatgaaat gggctttaac aaaacaagaa  3480
agaaacgtac ttaactgtgt gaagaaatgg aatcagcttt taataaaatt gacaacatt  3540
tattaccac                                                          3549
```